(12) United States Patent
Czyzewski et al.

(10) Patent No.: US 11,484,193 B2
(45) Date of Patent: Nov. 1, 2022

(54) NASAL SPECULUM

(71) Applicant: ANWIPHARMA SPÓLKA Z OGRANICZONA ODPOWIEDZIALNOSCIA, Niemcz (PL)

(72) Inventors: Piotr Czyzewski, Brzoza (PL); Michal Lawicki, Bydgoszcz (PL); Dariusz Sykutera, Bydgoszcz (PL)

(73) Assignee: ANWIPHARMA SPOLKA Z OGRANICZONA ODPOWIEDZIALNOSCIA, Niemcz (PL)

( * ) Notice: Subject to any disclaimer, the term of this patent is extended or adjusted under 35 U.S.C. 154(b) by 197 days.

(21) Appl. No.: 15/574,145

(22) PCT Filed: May 12, 2016

(86) PCT No.: PCT/PL2016/000054
§ 371 (c)(1),
(2) Date: Nov. 14, 2017

(87) PCT Pub. No.: WO2016/182464
PCT Pub. Date: Nov. 17, 2016

(65) Prior Publication Data
US 2018/0125347 A1    May 10, 2018

(30) Foreign Application Priority Data
May 14, 2015   (PL) .......................................... 412337

(51) Int. Cl.
*A61B 1/233*   (2006.01)
*A61B 1/32*   (2006.01)
(Continued)

(52) U.S. Cl.
CPC ................ *A61B 1/233* (2013.01); *A61B 1/32* (2013.01); *A61B 17/0206* (2013.01); *A61B 17/24* (2013.01)

(58) Field of Classification Search
CPC ..... A61B 17/0206; A61B 17/24; A61B 1/233; A61B 1/32
(Continued)

(56) References Cited

U.S. PATENT DOCUMENTS 730,284   A * 6/1903  Monosmith ........ A61B 17/0206
                                               600/219
3,815,607 A * 6/1974  Chester .................. A61B 17/30
                                               606/210
(Continued)

FOREIGN PATENT DOCUMENTS

EP          0777075 A1 *  6/1997  ............ F16L 33/025
GB          2 436 528 A      3/2007
(Continued)

*Primary Examiner* — Julian W Woo
(74) *Attorney, Agent, or Firm* — Andrzej Malarz, Esq.

(57) ABSTRACT

A nasal speculum, rhinoscope, designed for examination of the nasal cavity in both humans and animals, is characterized in that it is made from one piece of material and has a resilient arc-shaped connector (1) of the arms (2), said arms connected centrally to one another by means of a catch (3) located in opening (4), said arms extending beyond the said point of connection in the form of parallel shorter arms (5), said shorter arms terminating in appropriately shaped members (6) resembling a truncated cone, the speculum being also provided with a lip (7) positioning the arms of the speculum and with indentations (8) that prevent slipping of the hand when arms (2) are being pressed.

4 Claims, 3 Drawing Sheets

(51) Int. Cl.
*A61B 17/02* (2006.01)
*A61B 17/24* (2006.01)

(58) Field of Classification Search
USPC .................................................. 606/205, 210
See application file for complete search history.

(56) References Cited

U.S. PATENT DOCUMENTS

| | | | | |
|---|---|---|---|---|
| 5,366,459 A * | 11/1994 | Yoon | ................. | A61B 17/0057 |
| | | | | 606/151 |
| 5,772,582 A | 6/1998 | Huttner | | |
| 5,851,177 A | 12/1998 | Koch | | |
| 5,860,985 A * | 1/1999 | Anschutz | ............ | A61F 9/00736 |
| | | | | 606/107 |
| 5,921,990 A * | 7/1999 | Webb | ..................... | A61B 17/30 |
| | | | | 606/110 |
| 6,102,852 A * | 8/2000 | Liu | ......................... | A61B 1/32 |
| | | | | 600/219 |
| 9,556,988 B2 * | 1/2017 | Henrich | ................ | F16L 33/085 |
| 9,814,479 B2 * | 11/2017 | Mohmand | ............... | A61B 17/30 |
| 2002/0133060 A1 | 9/2002 | Doyle | | |
| 2006/0012199 A1 * | 1/2006 | Slank | ..................... | F16L 3/233 |
| | | | | 294/150 |

FOREIGN PATENT DOCUMENTS

| | | | |
|---|---|---|---|
| GR | 920100047 A | 10/1993 | |
| JP | H 08710 040 A | 3/1996 | |
| JP | 3026252 B2 | 3/2000 | |

* cited by examiner

NASAL SPECULUM

The invention relates to a nasal speculum, a rhinoscope, designed for examination of the nasal cavity, in both humans and animals.

Nasal specula were the subject of many dissertations and patent applications. Initially they were made of metal, while in recent decades they are also increasingly made of plastics. Initially the design of the majority of specula made use of the principle of a two-armed lever, where the arms were connected pivotally to each other at a point forming a common axis of rotation. Nowadays there are a number of speculum designs which also take advantage of the two-armed lever principle where, however, the ends of the arms are connected to each other and a connector fulfils the function of the pivot.

Specula made of metal are certainly durable, made with due precision and are reusable. However, they require sterilization after each use. The design of specula made of plastic or of other flexible material is much simpler, and such items are usually designed for single use.

The first disclosed patent applications concerning specula date from the beginnings of the past century, e.g. U.S. Pat. No. 730,284 from 1903.

The Greek patent specification no. GR 920100047 describes a nasal speculum that combines the advantages of both of the above solutions, as that speculum has a durable metal body and replaceable disposable tips made of plastic.

Disposable specula should be of simple design and at the same time ensure reliable operation during medical examination, and should preferably be made of one piece of material. Efforts to conceive such instruments led to the emergence of just such designs.

U.S. Pat. No. 6,102,852 describes a speculum which includes two arms known from metal designs wherein the traditional pivot is replaced with a resilient connector.

Specula known form patent specifications: Japanese JP3026252 and American U.S. Pat. No. 5,772,582, are made of plastic and have crossing arms with appropriately shaped tips resembling truncated cones. Squeezing the arms makes the tips to move apart in the opposite direction.

Another interesting solution, though very complex, is that described in U.S. Pat. No. 5,851,177.

A disadvantage of the above-described designs is the relatively large weight and size of the speculum, which undoubtedly translates into increased consumption of materials and higher costs of storage and transportation.

Due to the lack of an arms connecting member near the tips thereof, there is an additional disadvantage consisting in that in the open position the tips of the arms are positioned asymmetrically in the plane of longitudinal section of the instrument. The effect thereof is the obvious lack of comfort during the examination for both the patient and the physician.

The speculum made of one piece of plastic, disclosed in Japanese patent JP871040, provided with a pivot with a common axis of rotation but arranged asymmetrically on only one side of the instrument, enables better control of spreading the tips than in the case of crossing arms, but still it does not eliminate the disadvantages of non-parallel arrangement of the tips in the open position.

The object of the invention is to provide a speculum characterized by low weight and small size, convenient in storage and transport, and ensuring parallel position of the tips at every stage of spreading thereof.

The essence of the speculum design according to the invention is that the instrument is provided with a resilient connector of arms connected centrally in the upper part by means of a catch, which results in smooth and symmetrical spreading of the tips of the arms in the plane of longitudinal section, wherein the entire instrument is made from one piece of material.

The subject of the invention is illustrated by an embodiment shown in drawings, of which:

Figure 1:
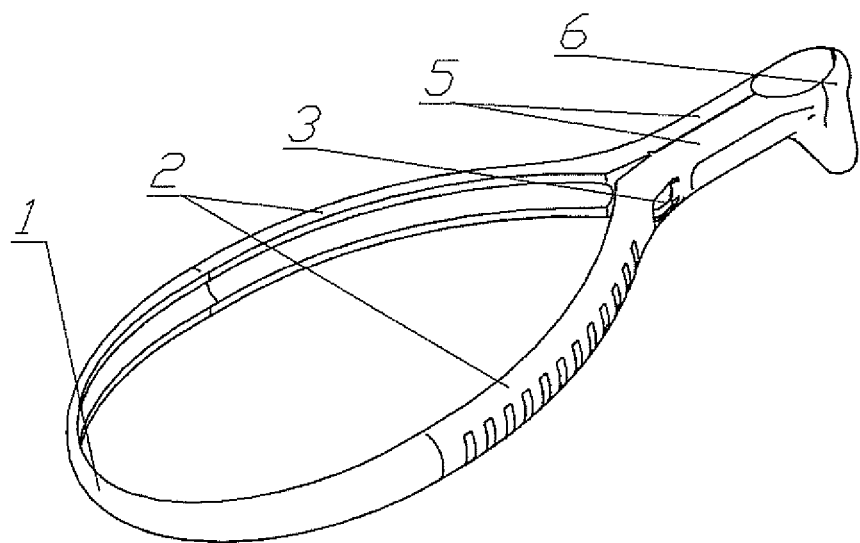
FIG. 1 shows a perspective view of the speculum.
Figure 2:
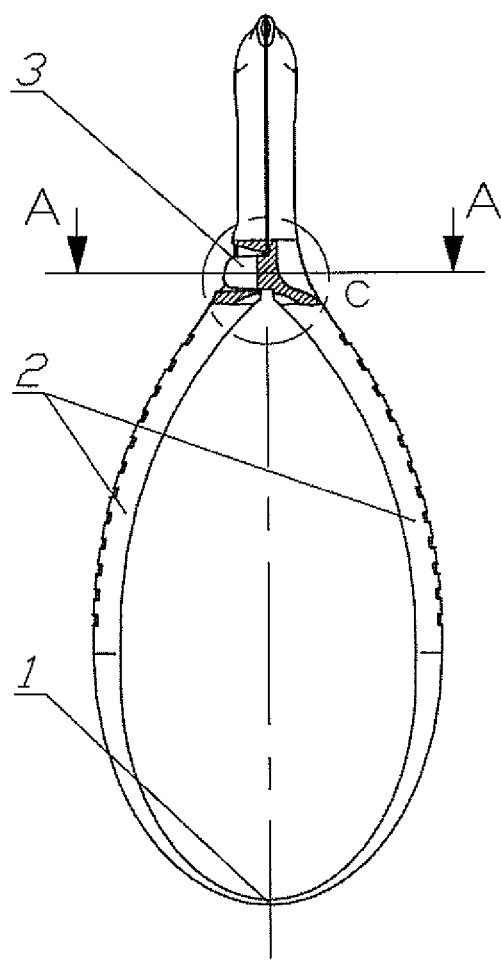
FIG. 2 shows top view of the speculum and its partial longitudinal section C in the area of the joint between the arms.
Figure 3:
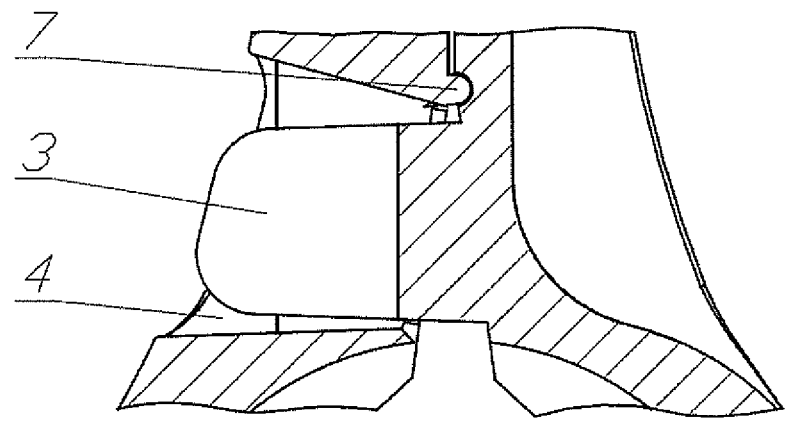
FIG. 3 shows enlarged view of the longitudinal section C.
Figure 4:
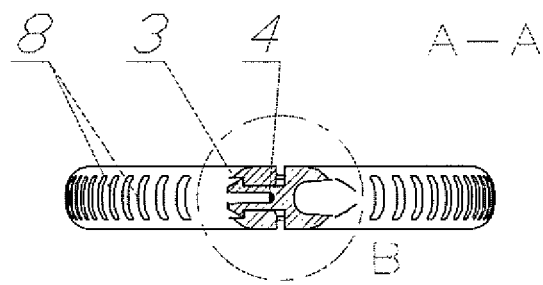
FIG. 4 shows cross section A-A in the area of the joint between the arms.
Figure 5:
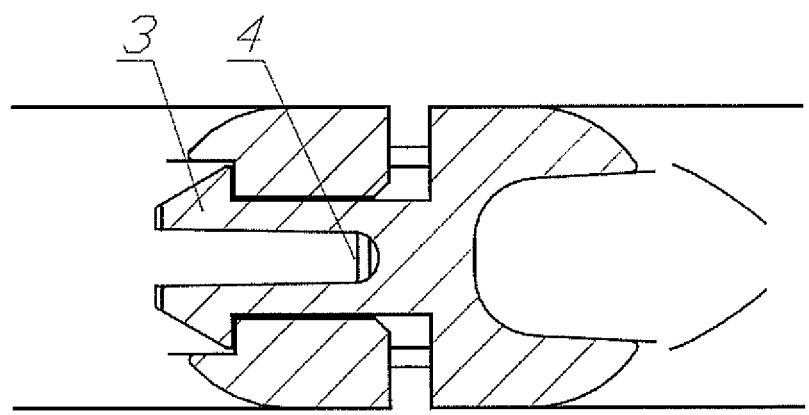
FIG. 5 shows enlarged view of the cross section A-A.
Figure 6:
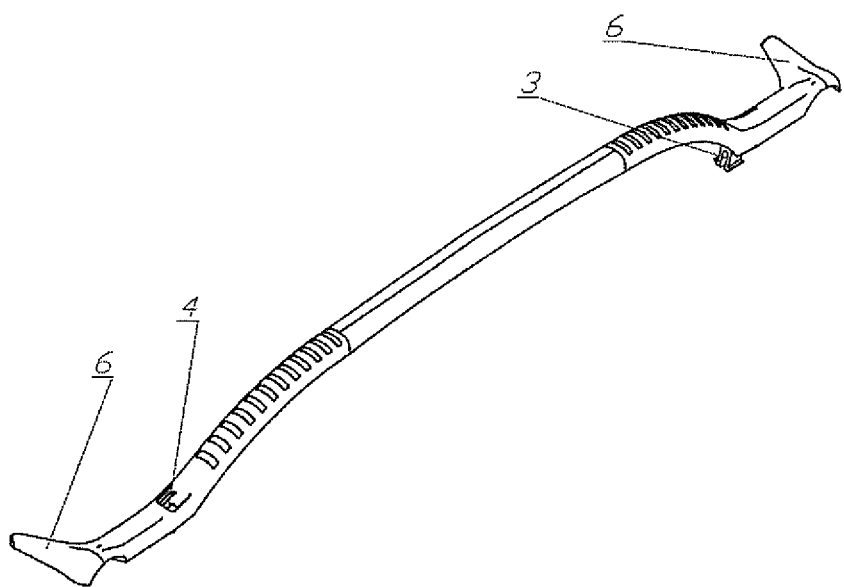
FIG. 6 shows a perspective view of the disassembled speculum looking from outside.
Figure 7:
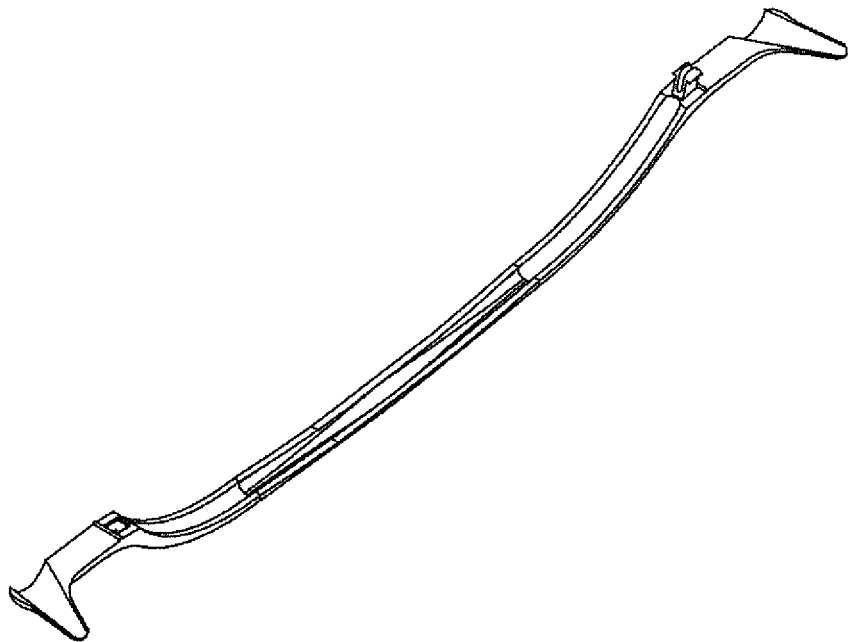
FIG. 7 shows a perspective view of the disassembled speculum looking from inside.

The speculum according to the invention, assembled and ready to use, has a resilient arc-shaped connector 1 of the arms 2, said arms connected centrally to one another by means of a catch 3 located in opening 4, said arms extending beyond the said point of connection in the form of parallel shorter arms 5, said shorter arms terminating in appropriately shaped members 6 resembling a truncated cone, the speculum being also provided with a lip 7 positioning the arms and with indentations 8 that prevent slipping of the hand when arms 2 are being pressed.

The speculum according to the invention is made from one piece of material, which contributes to material saving, enables complete automation of sterile manufacturing process, and facilitates storage and transport.

Carefully fabricated, smooth and rounded tips of the speculum, and the precise arms that spread in one plane and the ergonomically contoured longer arms of the speculum allow for smooth and accurate manipulating of the tips of the disposable speculum and improve the comfort of the examination.

The invention claimed is:

1. A nasal speculum made of a single piece of material, comprising:
   springy, ergonomically contoured arms connected by a resilient connector in a shape of an arc in a lower part of the speculum, said arms being connected centrally to each other at a connection point in an upper part of the speculum by a catch located in an opening, wherein a part of the arms extending beyond the connection point forms parallel shorter arms terminated by members in a shape of a truncated cone,
   a protruding lip adjacent to the opening for positioning the speculum arms, recesses configured to engage the lip, and
   indentations that prevent slipping of a hand when the arms are being pressed, wherein
   the arms being connected centrally in the upper part of the speculum by the catch located in the opening results in smooth and symmetrical spreading of rounded tips of the arms in a plane of a longitudinal section, wherein
   the speculum allows ends of the speculum to open after pressure is applied substantially at any point of the arms, wherein
   the speculum is delivered unfolded, wherein
   the speculum is a disposable device which cannot be unfolded again due to the catch, wherein the catch located in the opening and the lip engaged with the recesses form a pivot joint between the parallel shorter arms and the lower part of the speculum.

2. The nasal speculum according to claim 1, wherein the parallel shorter arms are laid out in a single plane.

3. The nasal speculum according to claim 1, wherein the arms are spreadable in one plane, wherein the tips are in parallel position at every stage of spreading, and wherein the tips of the speculum are smooth.

4. A nasal speculum made of a single piece of material, and comprising: arms with indentations the arms being connected in a lower part of the speculum by a resilient connector, and the arms in an upper part of the speculum being terminated by members in a shape of truncated cone, wherein the resilient connector has a shape of an arc, wherein the arms are connected centrally to each other at a connection point in the upper part of the speculum by a catch located in an opening, wherein a part of the arms extending beyond the connection point forms parallel shorter arms, wherein the speculum is provided with a protruding lip adjacent to the opening and recesses adjacent to the catch for positioning the arms of the speculum, and wherein the catch in the opening and the lip engaged with the recesses allow the parallel shorter arms to pivot relative to the lower part of the speculum.

\* \* \* \* \*